United States Patent
Dale et al.

(10) Patent No.: US 8,283,344 B2
(45) Date of Patent: Oct. 9, 2012

(54) METHOD OF TREATING INHERITED SEVERE NEUTROPENIA

(75) Inventors: David C. Dale, Seattle, WA (US); Paul E. Finke, Milltown, NJ (US); Richard A. Mumford, Red Bank, NJ (US); Andranik Andrew Aprikyan, Kenmore, WA (US)

(73) Assignees: Merck & Co., Inc., Rahway, NJ (US); University of Washington, Seattle, WA (US)

( * ) Notice: Subject to any disclaimer, the term of this patent is extended or adjusted under 35 U.S.C. 154(b) by 174 days.

(21) Appl. No.: 12/673,588

(22) PCT Filed: Sep. 5, 2008

(86) PCT No.: PCT/US2008/010430
§ 371 (c)(1),
(2), (4) Date: Feb. 16, 2010

(87) PCT Pub. No.: WO2009/035541
PCT Pub. Date: Mar. 19, 2009

(65) Prior Publication Data
US 2011/0059960 A1      Mar. 10, 2011

Related U.S. Application Data

(60) Provisional application No. 60/993,253, filed on Sep. 10, 2007.

(51) Int. Cl.
*A01N 43/00* (2006.01)
*A61K 31/397* (2006.01)
*A61K 31/407* (2006.01)

(52) U.S. Cl. ......... 514/210.18; 514/255.01; 514/252.14; 514/233.8

(58) Field of Classification Search ............ 514/210.18, 514/233.8, 255.01
See application file for complete search history.

(56) References Cited

U.S. PATENT DOCUMENTS

| | | |
|---|---|---|
| 5,229,381 A | 7/1993 | Doherty et al. |
| 6,194,569 B1 | 2/2001 | Sheeran et al. |
| 2005/0260140 A1 | 11/2005 | White et al. |

OTHER PUBLICATIONS

Aprikyan, et al. "Diversity and molecular modeling of neutrophil elastase mutations in patients with severe congenital neutropenia and acute myelogenous leukemia." Blood, 2004, vol. 104, No. 11, Part 1, pp. 407A.

Missen, et al. "Stage specific gene expression of serpins and their cognate proteases during myeloid differentiation." British Journal of Haematology, 2006, vol. 135, No. 5, pp. 715-724.

*Primary Examiner* — Brandon Fetterolf
*Assistant Examiner* — Shirley V Gembeh
(74) *Attorney, Agent, or Firm* — Maria V. Marucci; Valerie J. Camara

(57) ABSTRACT

The invention is directed to a method of treating severe neutropenia, and in particular, cyclic neutropenia (CN) or severe congenital neutropenia (SCN), in a patient in need of such treatment comprising: administering a therapeutically effective amount of a compound of Formula (I) or a pharmaceutically acceptable salt thereof.

9 Claims, No Drawings

METHOD OF TREATING INHERITED SEVERE NEUTROPENIA

CROSS-REFERENCE TO RELATED APPLICATION

This application claims priority from U.S. Provisional Application No. 60/993,253, filed Sep. 10, 2007.

This invention was made with government support under CA089135 awarded by National Institutes of Health (NIH). The government has certain rights in the invention.

CROSS REFERENCE TO RELATED APPLICATIONS

This application is a U.S. National Phase application under 35 U.S.C. §371 of PCT Application No. PCT/US2008/010430, filed Sep. 5, 2008 which claims priority under 35 U.S.C. §119(e) from U.S. Provisional Application Ser. No. 60/993,253 filed Sep. 10, 2007.

BACKGROUND OF THE INVENTION

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodontitis, cystic fibrosis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., J. Biol. Chem., 255, 9848 (1980); and (3) There is an appearance and/or presence of lymphoid cells, macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" Sci. Am. Jul. 1974, pp. 74-88). For example, one of the natural inhibitors, .alpha.sub.1-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, TIBS, 211 (1976).

Applicants have surprisingly discovered that inhibitors of neutrophil elastase, and in articular, elastase inhibitors of Formula I, may be useful in the treatment of severe neutropenia, especially, cyclic neutropenia (CN) or severe congenital neutropenia (SCN) attributable to mutations in the neutrophil elastase (NE, ELA2) gene.

Severe congenital neutropenia (SCN) is a hematopoietic disorder characterized by maturation arrest at the promyelocytic stage of differentiation, recurring infections, and evolution to acute myeloid leukemia. Mutations in either the neutrophil elastase (NE) gene (sporadic or autosomal dominant SCN) or in the HAXI gene (sporadic or autosomal recessive SCN) lead to a similar clinical phenotype and similar morphological changes of "maturation arrest" in the marrow. Most studies now indicate that maturation arrest in SCN is attributable to accelerated apoptosis of myeloid progenitor cells triggered by the mutant gene products. Cyclic neutropenia (CN) is a hematopoietic disorder also characterized by recurring severe infections and regular oscillations of blood neutrophils from zero to near normal level. These patients also have mutations in the neutrophil elastase gene and also exhibit accelerated apoptosis of bone marrow myeloid progenitor cells.

We have established a model of SCN with doxycycline-regulated expression of del.145-152 mutant NE in human promyelocytic tet-off HL-60 cells. The ratio of normal-to-mutant NE products is approximately 1:1, which is expected in SCN patients with heterozygous mutation. Expression of mutNE in promyelocytic cells resulted in a block of myeloid differentiation with ~70% reduction in differentiated neutrophils similar to that observed in SCN. The reduced cell growth and accelerated apoptosis were also observed in response to mutNE expression. Thus, this cellular model of SCN appears to closely recapitulate the human phenotype. The elastase-specific activity in cells expressing mutNE was approximately 40% higher than in control cells suggesting that mutNE exhibits at least some proteolytic activity. Screening this SCN model with various agents revealed a cell-permeable proprietary NE-specific small molecule inhibitor, Compound 242, disclosed hereinunder, which inhibited the NE activity by more than 80%. Data thus far indicate that treatment of HL-60 cells expressing the del.145-152 mutNE with Compound 242 led to complete restoration of cell growth and increased myeloid differentiation in these cells. Inhibition of NE activity did not reduce the growth rate of control cells expressing normal elastase. These data confirm our belief that the NE-specific inhibitor Compound 242 and the other compound of Formula I as disclosed hereinunder are useful for the treatment of patients with SCN or CN attributable to mutant NE.

SUMMARY OF THE INVENTION

The invention is directed to a method of treating severe neutropenia, especially, cyclic neutropenia (CN) or severe congenital neutropenia (SCN), in a patient in need of such treatment comprising: administering a therapeutically effective amount of a compound of Formula (I)

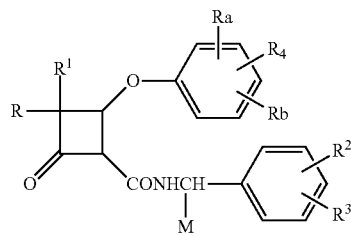

or a pharmaceutically acceptable salt thereof.

DETAILED DESCRIPTION OF THE INVENTION

In one embodiment, the invention is directed to a method of treating cyclic or severe congenital neutropenia, in a patient in need of such treatment comprising: administering a therapeutically effective amount of an elastase inhibitor.

In another embodiment, the invention is directed to a method of treating cyclic or severe congenital neutropenia, in a patient in need of such treatment comprising: administering a therapeutically effective amount of an elastase inhibitor, wherein said elastase inhibitor is capable of penetrating the cell membrane of the neutrophils and neutrophil precursors in said patient and thereafter inhibits the elastase within said cells.

In another embodiment the invention is directed to a method of treating severe neutropenia, and in particular, cyclic or severe congenital neutropenia (CN or SCN), in a patient in need of such treatment comprising: administering a therapeutically effective amount of a compound of Formula (I)

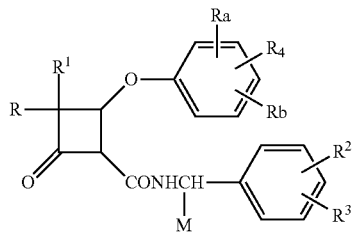

or a pharmaceutically acceptable salt thereof wherein
$R^1$ is $C_{1-6}$ alkyl or $C_{1-6}$ alkoxy-$C_{1-6}$alkyl;
M is
(1) hydrogen,
(2) $C_{1-6}$alkyl,
(3) hydroxy $C_{1-6}$alkyl,
(4) halo $C_{1-6}$alkyl,
(5) $C_{2-6}$alkenyl, or
(6) $C_{1-6}$alkoxy-$C_{1-6}$alkyl;
Ra and Rb are each individually
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) di-($C_{1-6}$alkylamino;
(9) hydroxy;
$R_2$ and $R_3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino$C_{2-3}$alkyloxy carbonyl wherein the amino is optionally mono or di-substituted with $C_{1-6}$alkyl,
(9) amino$C_{2-3}$alkylamino carbonyl wherein the amino is optionally mono or di-substituted with $C_{1-6}$ alkyl,
(10) hydroxy,
(11) aminocarbonyl wherein the amino is optionally mono or di-substituted with $C_{1-6}$alkyl,
(12) hydroxymethyl,
(13) aminocarbonyloxy $C_{1-3}$alkyloxy wherein the amino is optionally mono or di-substituted with $C_{1-6}$ alkyl,
(14) cyano,
(15) morpholinocarbonylphenyl,
(16) amino wherein the amino is optionally mono or di-substituted with $C_{1-6}$alkyl, with the proviso that $R_2$ and $R_3$ may be joined together to form a methylenedioxy group or a furan ring,
(17) morpholinocarbonyl;
R4 is
(a) Q-C(O)—Y—N(R7)(R8), or
(b) Q-C(O)—ORx, where Rx is carboxyC-16alkyl, benzyloxycarbonyl$C_{1-3}$ alkyl, or t-butoxycarbonyl$C_{1-3}$alkyl,
wherein
Q is a covalent bond or —$C(R_5)(R_6)$—
wherein $R_5$ and $R_6$ are each individually $C_{1-3}$ alkyl or hydrogen, Y is

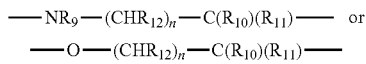

or a covalent bond;
$R_{12}$ is hydrogen or $C_{1-3}$alkyl;
$R_7$ and $R_8$ are each individually
(a) hydrogen,
(b) $C_{1-6}$alkyl,
(c) $C_{1-6}$alkyloxy $C_{2-3}$alkyl,
(d) hydroxy $C_{2-6}$alkyl,
(e) polyhydroxy$C_{2-6}$alkyl,
(f) carboxamido $C_{2-6}$alkyl,
(g) polyacyloxy$C_{2-6}$alkyl
(h) $C_{1-6}$alkanoyl,
(i) substituted phenyl or phenyl $C_{1-6}$alkyl, wherein the substituent is $X_1$ as defined immediately below,
(j) $C_{2-6}$alkenyl,
(k) $C_{6-10}$cycloalkenyl,
(l) heteroaryl $C_{1-6}$alkyl wherein the hetero aryl includes pyridinyl, imidazolyl, triazolyl, benzylimidazolyl, and furyl,
(m) carboxy $C_{1-6}$alkyl,
(n) carbo $C_{1-6}$alkoxy $C_{1-3}$alkyl,
(o) phenylsulfonyl,
(p) $C_{1-6}$alkylsulfonyl,
(q) benzyloxy,
(r) morpholinyl $C_{1-3}$alkylsulfonyl,
(s) tetrahydropyranyl,
(t) amino$C_{1-3}$alkylsulfonyl wherein the amino is optionally mono or di-substituted with $C_{1-6}$alkyl,
(u) aminocarbonyl wherein the amino is optionally mono or di-substituted with $C_{1-6}$alkyl,
(v) aminocarbonyloxy$C_{2-6}$alkyl wherein the amino is optionally mono or di-substituted with $C_{1-6}$alkyl,
(w) azabicyclo of 7 to 12 atoms,
(x) di $C_{1-3}$alkylamino $C_{2-6}$alkyl wherein the amino is optionally mono or di-substituted with $C_{1-6}$alkyl,
(y) bicycloalkyl of 7 to 12 atoms,
(z) $C_{3-10}$cycloalkyl optionally substituted with $C_{1-6}$alkyl,
(aa) pyrazolidinyl,
(bb) substituted piperidinyl or pyrrolidinyl wherein the substituent is hydrogen, $C_{1-3}$alkyl, hydroxy$C_{1-3}$ alkylbenzyl, carboxamido or amino wherein the amino is optionally mono or di-substituted with $C_{1-6}$ alkyl,
(cc) substituted pyrrolidinyl wherein the substituent is carboxamido or amino wherein the amino is optionally mono or di-substituted with $C_{1-6}$alkyl,
(dd) pyrimidinyl,
(ee) N-cyano-N'-phenylamidino,
(ff) phosphono$C_{1-6}$alkyl, or
(gg) α-$C_{1-3}$alkyl benzyl or mono or di-substituted benzyl or mono or di-substituted pyridylmethyl, wherein the substituents are $X_1$ and $X_2$,
wherein
$X_1$ is
(1) hydrogen,
(2) halo,
(3) $C_{1-6}$alkyl,
(4) halo-$C_{1-6}$alkyl,
(5) $C_{2-6}$alkenyl,
(6) hydroxy-$C_{1-6}$alkyl,
(7) $C_{1-6}$alkyl carbonyl,
(8) $C_{1-6}$alkylcarbonylamino;
(9) CN,
(10) $CF_3$,
(11) $CH_3O$,
(12) amino wherein the amino is optionally mono or di-substituted with $C_{1-6}$ alkyl;
(13) carboxy, or
(14) phenylsulfonylaminocarbonyl;
$X_2$ is hydrogen, halo or $C_{1-6}$alkyl;
n is 1, 2, 3, 4 or 5;
$R_9$ is selected from hydrogen, $C_{1-4}$alkyl, and $C_{1-3}$alkoxy$C_{1-3}$alkyl; or phenyl, phenyl $C_{1-3}$alkyl, pyridyl, and pyridyl $C_{1-3}$alkyl;
$R_{10}$ and $R_{11}$ are each independently selected from hydrogen, $C_{1-4}$alkyl, and $C_{1-3}$ alkoxy$C_{1-3}$alkyl, or aryl as defined above, or are together oxo; or
wherein $R_7$ and $R_8$ are joined together to form mono or di-substituted ring of 4, 5, 6, or 7 atoms or 7 to 12 atoms such as
(1) piperidinyl or homopiperdinyl,
(2) piperazinyl,
(3) morpholinyl, thiomorpholinyl or 1,1-dioxo-4-thiomorpholinyl,
(4) pyrroylidinyl,
(5) pyrryl,
(6) imidazolyl,
(7) triazolyl,
(8) saturated azabicyclo of 7 to 12 atoms,
(9) azaspiro having 3 to 9 carbon atoms, said ring being saturated,
(10) tetrazolyl,
(11) pyrazolidinyl,
(12) dihydodimethozyisoquinolyl,
(13) azetidinyl, or
(14) diazabicyclo ring of 7-12 atoms,
wherein the substituents are each selected from the group consisting of hydrogen and $C_{1-3}$alkyl, benzyloxycarbonyl, carboxy, phenyl $C_{1-3}$alkyl amino carbonyl, pyrrolidinylmethyl, hydroxy $C_{1-3}$ alkyl, $C_{1-6}$ alkyloxy, $C_{1-4}$alkyloxy carbonyl, aminocarbonyl wherein the amino is optionally mono or di-substituted with $C_{1-6}$ alkyl, and oxo; or
—N(R7)R8 may be an amino acid residue including natural amino acids such as lysine; or $R_8$ and $R_9$ are joined together to form a mono or di-substituted saturated monocyclic ring of 6 to 7 atoms and having two hetero atoms which are the nitrogens to which $R_8$ and $R_9$ are attached; said rings to include piperazinyl and homopiperazinyl; or $R_9$ and $R_{10}$ are joined together to form a mono or di-substituted monocyclic saturated ring of 5 to 7 atoms and having one hetero atom which is the nitrogen to which $R_9$ is attached; or
wherein $R_9$ and $R_{12}$ are joined together to form a mono or di-substituted saturated monocyclic ring of 5, 6; or 7 atoms, said ring having one hetero atom which is the nitrogen to which $R_9$ is attached; or wherein $R_{10}$ and $R_{12}$ are joined together to form a mono or di-substituted saturated monocyclic ring of 5, 6, or 7 carbon atoms; or
wherein $R_8$ and $R_{11}$ are joined together to form a mono or di-substituted saturated monocyclic ring of 5, 6, or 7 atoms, said ring having one hetero atom which is the nitrogen to which $R_8$ is attached; and the substituents are independently selected from Hydrogen and $C_{1-3}$alkyl.

These compounds, their method of preparation and other utilities are disclosed in U.S. Pat. No. 5,474,485, issued May 5, 1998, which is hereby incorporated by reference.

As appreciated by those of Skill in the art the term "alkyl" such as in C.sub.1-6 alkyl, includes, methyl, ethyl, propyl, butyl, pentyl, and hexyl, and where appropriate, branched chained forms including isopropyl and tert-butyl.

As may also be appreciated by those of skill in the art, the spacer

in definition Y, may, in the alternative be placed to the right of $C(R_{10})(R_{11})$.

As may also be appreciated, the group —$N(R_7)(R_8)$ may also be oxidized to the corresponding oxide.

In one Class the instant invention is directed to the compounds of the Formula (I) and pharmaceutically acceptable salts thereof wherein: R is $C_{1-6}$alkyl;

$R_1$ is $C_{1-6}$alkyl or $C_{1-6}$alkoxy-$C_{1-6}$alkyl;

M is
(1) hydrogen,
(2) $C_{1-6}$alkyl,
(3) hydroxy $C_{1-6}$ alkyl,
(4) halo $C_{1-6}$alkyl,
(5) $C_{2-6}$alkenyl, or
(6) $C_{1-6}$ alkoxy-$C_{1-6}$alkyl;

Ra is
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di-substituted with $C_{1-6}$alkyl;

Rb is hydrogen, or $C_{1-6}$alkyl, $R_2$ and $R_3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di-substituted with $C_{1-6}$alkyl, or with the proviso that $R^2$ and $R^3$ may be joined together to form a methylenedioxy group or a furan ring;

R4 is
(a) Q-C(O)—Y—N(R7)(R8), or
(b) Q-C(O)—ORx, where Rx is carboxyC-16alkyl, benzyloxycarbonyl$C_{1-3}$ alkyl, or t-butoxycarbonyl$C_{1-3}$alkyl,
wherein
Q is a covalent bond or —$C(R_5)(R_6)$—
wherein $R_5$ and $R_6$ are each individually $C_{1-3}$ alkyl or hydrogen,
Y is

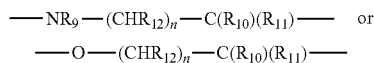

or a covalent bond;
$R_{12}$ is hydrogen or $C_{1-3}$alkyl;
$R_7$ and $R_8$ are each individually
(a) hydrogen,
(b) $C_{1-6}$alkyl,
(c) $C_{1-6}$alkyloxy $C_{2-3}$alkyl,
(d) hydroxy $C_{2-6}$alkyl,
(e) carboxamido $C_{1-6}$alkyl,
(f) $C_{1-6}$alkanoyl,
(g) substituted phenyl or phenyl $C_{1-6}$alkyl wherein the substituents are $X_1$, and $X_2$
(h) $C_{2-6}$alkenyl,
(i) $C_{6-10}$cycloalkenyl,
(j) heteroaryl $C_{1-6}$ alkyl wherein the hetero aryl includes pyridinyl, imidazolyl, triazolyl, benzylimidazolyl, and furyl,
(k) carboxy $C_{1-6}$ alkyl,
(l) $C_{1-6}$alkylsulfonyl,
(m) carbo$C_{1-6}$ alkyloxy$C_{2-3}$alkyl,
(n) morpholinyl $C_{1-3}$alkylsulfonyl,
(o) amino$C_{1-3}$alkylsulfonyl wherein the amino is optionally mono or di-substituted with $C_{1-6}$alkyl,
(p) aminocarbonyl wherein the amino is optionally mono or di-substituted with $C_{1-6}$ alkyl,
(q) aminocarbonyloxy$C_{1-6}$alkyl wherein the amino is optionally mono or di-substituted with $C_{1-6}$alkyl,
(r) di $C_{1-3}$alkylamino $C_{1-6}$ alkyl wherein the amino is optionally mono or di-substituted with $C_{1-6}$alkyl,
(s) pyrazolidinyl,
(t) substituted piperidinyl as defined above,
(u) substituted pyrrolidinyl as defined above,
(v) pyrimidinyl,
(w) benzyloxy,
(x) $C_{3-10}$cycloalkyl,
(z) α-$C_{1-3}$ alkyl benzyl or mono or di-substituted benzyl or mono or di-substituted pyridylmethyl, wherein the substituents are $X_1$ and $X_2$,
wherein
$X_1$ is
(1) hydrogen,
(2) halo,
(3) $C_{1-6}$alkyl,
(4) halo-$C_{1-6}$alkyl,
(5) $C_{2-6}$alkenyl,
(6) hydroxy-$C_{1-6}$alkyl,
(7) $C_{1-6}$alkylcarbonyl,
(8) $C_{1-6}$alkylcarbonylamino;
(9) di-$C_{1-3}$alkylamino; or
(10) carboxy,
$X_2$ is hydrogen, halo or $C_{1-6}$alkyl;
n is 1, 2, 3, 4 or 5;
$R_9$ is selected from hydrogen, $C_{1-4}$alkyl, and $C_{1-3}$alkoxy$C_{1-3}$alkyl; $R_{10}$ and $R_{11}$ are each independently selected from hydrogen, $C_{1-4}$alkyl, and $C_{1-3}$alkoxy $C_{1-3}$alkyl; or
wherein $R_7$ and $R_8$ are joined together to form mono or di-substituted ring of 4, 5, 6, or 7 atoms such as
(1) piperidinyl,
(2) piperazinyl,
(3) morpholinyl,
(4) pyrroylidinyl,
(5) pyrryl,
(6) imidazolyl,
(7) triazolyl,
(8) tetrazolyl,
(9) pyrazolidinyl,
(10) azetidinyl,
wherein the substituents are each selected from the group consisting of hydrogen and $C_{1-3}$alkyl, benzyloxycarbonyl, carboxy, phenyl $C_{1-3}$alkyl amino carbonyl, pyrrolidinyl, methyl, hydroxy $C_{1-3}$alkyl, $C_{1-6}$alkyloxy, $C_{1-4}$alkyloxy carbonyl, and oxo; or $R_8$ and $R_9$ are joined together form a saturated ring of 5 to 7 atoms and having two hetero atoms; or $R_9$ and $R_{10}$ are joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or wherein $R_8$ and $R_{11}$ are joined together to form a ring of 5, 6, or 7 atoms, said ring being saturated and having one hetero atom.

In one subclass, the invention concerns compounds of Formula I wherein
R is $C_{1-3}$alkyl;
$R_1$ is $C_{1-3}$alkyl;
M is
(a) $C_{1-6}$alkyl, or
(b) $C_{2-6}$ alkenyl;
$R_2$ is
(a) hydrogen,
(b) $C_{1-6}$ alkyl, or $C_{1-6}$alkoxy, and
$R^3$ is hydrogen, or $R_2$ and $R^3$ are joined together to form a methylenedioxy group or a furan ring;
$R_5$ and $R_6$ are each individually hydrogen or $C_{1-3}$alkyl;
$R_7$ and $R_8$ are each independently selected from
(a) hydrogen,
(b) $C_{1-3}$alkyl,
(c) $C_{1-3}$ alkoxy $C_{2-3}$alkyl,
(d) $C_{3-7}$cycloalkyl,
(e) hydroxy$C_{2-3}$alkyl,
(d) carbo $C_{1-4}$alkyloxymethyl,
(g) substituted benzyl wherein the substituents are $X_1$ and $X_2$ wherein $X_1$ is hydrogen and $X_2$ is
(1) hydrogen,
(2) halo, or
(3) $C_{1-3}$alkyl;
n is 1, 2 or 3, and
$R_9$, $R_{10}$ and $R_{11}$ are each independently selected from hydrogen, $C_{1-4}$alkyl, and $C_{1-3}$alkoxy $C_{1-3}$alkyl; or
$R_7$ and $R_8$ are joined together to form a substituted ring selected from
(a) piperidinyl,
(b) piperazinyl, and
(c) morpholinyl;
or
$R_8$ and $R_9$ are joined together to form a ring of 6 to 7 atoms and having two hetero atoms; $R_9$ and $R_{10}$ re joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or
wherein $R_8$ and $R_{11}$ are joined together to form a ring of 5, 6, or 7 atoms, said ring being saturated and having one hetero atom.

In a narrower sub-class are the compounds wherein
Q is a covalent bond;
R is methyl or ethyl;
$R_1$ is methyl or ethyl;
M is
(a) $C_{1-4}$alkyl, or
(b) $C_{2-3}$alkenyl;
$R^2$ is
(a) hydrogen,
(b) $C_{1-3}$ alkyl, or $C_{1-3}$alkoxy, and
$R^3$ is hydrogen, or
$R^2$ and $R^3$ are joined together to form a furan or dioxacyclopentane ring;
n is 1 or 2;
$R_9$ and $R_{10}$ are each independently selected from
(a) $C_{1-3}$alkyl,
(b) $C_{1-3}$ alkoxy $C_{1-3}$ alkyl,
(c) hydrogen, $R_7$ and $R_8$ are each independently selected from
(a) $C_{1-3}$ alkyl,
(b) $C_{1-3}$alkoxy $C_{2-3}$alkyl,
(c) hydrogen,
(d) hydroxyethyl,
(e) carboethoxymethyl,
(f) cyclopropyl,
or
$R_7$ and $R_8$ are joined together to form a substituted ring selected from
(a) piperidinyl, and
(b) morpholinyl, or
$R_8$ and $R_9$ are joined together to form a piperazine ring.

Illustrating the invention is the following two tables of compounds:

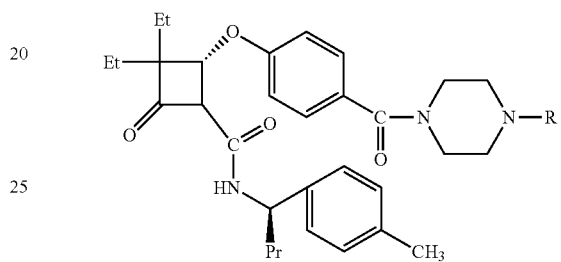

| No. | R | Kobs/[I] |
|---|---|---|
| 242 | —CH3 | 1,700,000 |
| 243 | 4-fluorophenyl | 7,486,000 |
| 244 | 3-chlorophenyl | 2,453,000 |
| 245 | Phenyl | 5,276,000 |
| 246 | Benzyl | 5,171,000 |
| 247 | H | 1,100,000 |
| 248 | i-propyl | 2,392,000 |
| 249 | i-butyl | 2,476,000 |
| 250 | —CH$_2$CO$_2$Et | 1,571,000 |
| 251 | —CH$_2$CO$_2$H | 1,947,000 |
| 252 | Et | 2,324,000 |
| 253 | Pr | 1,768,000 |
| 254 | 2-pyrimidinyl | 2,143,000 |
| 255 | —CH$_2$CH$_2$OC(O)NHCH$_3$ | 2,548,000 |
| 256 | Cyclopropyl | 3,587,000 |
| 256a | —CH$_2$CH$_2$OH | 2,000,000 |

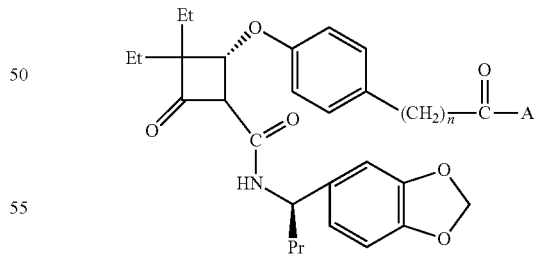

| No. | n | R | Kobs/[I] |
|---|---|---|---|
| 257 | 1 | —NH$_2$ | 2,342,000 |
| 258 | 1 | 4-morpholinyl | 1,785,000 |
| 259 | 1 | —N(CH$_3$)CH$_2$CH$_2$N(CH$_3$)$_2$ | 2,522,000 |
| 260 | 0 | —N(CH$_3$)CH$_2$CH$_2$N(CH$_3$)$_2$ | 3,317,000 |
| 261 | 0 | —N(Et)$_2$ | 3,207,000 |
| 262 | 0 | —N(CH$_3$)(n-butyl) | 3,125,000 |
| 263 | 0 | 4-methyl-1-piperazinyl | 3,805,000 |
| 264 | 0 | —N(CH$_3$)CH$_2$CH$_2$N(CH$_3$)CH$_2$Ph | 3,427,000 |
| 265 | 0 | —CH$_2$CO$_2$Et | 4,500,000 |

-continued

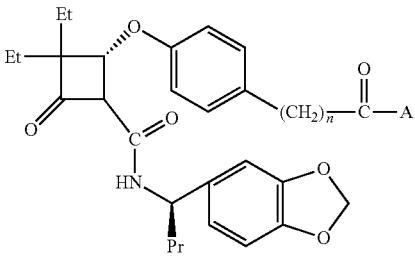

| No. | n | R | Kobs/[I] |
|---|---|---|---|
| 265a | 0 | 1-piperazinyl | 3,250,000 |
| 265c | 0 | 4-(2-hydroxyethyl)-1-piperazinyl | 4,800,000 |
| 265d | 0 | 4-morpholinyl | 3,700,000 |

Enzyme Assays for the Inhibition of Human Polymorphonuclear Leukocyte Elastase Via Hydrolysis of N-t-Boc-alanyl-alanyl-prolylalanine-p-nitroanilide (Boc-AAPAN) or N-t-Boc-alanyl-prolylvaline-p-nitroanilide (Boc-AAPVN) Reagent:
  0.05M TES (N-tris[hydroxymethyl]methyl-2-minoethanesulfonic acid) Buffer, pH 7.5.
0.2 mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01-0.1 ml of DMSO with or without inhibitor was added. After mixing, a measurement was taken at 410 m.mu. to detect any spontaneous hydrolysis due to presence of test compound. 0.05 Milliliters of PMN extract was then added and the ΔOD/min at 410 m.mu. was measured and recorded. Beckman model 35 spectrophotometer was used.

Results were expressed to the nearest thousand k obs/I which is the second order rate constant in per mole per second for inactivation of the enzyme.

The elastase activity in the crude PMN extract may vary from one preparation to another. A control of each new batch is run, and the volume added in the assay procedure is adjusted according to activity.

For treatment as described above the compounds of Formula (I) may be administered orally, topically, parenterally, by inhalation spray or rectally in dosage unit Formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution glucose in water and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient(s) that may be combined with the carrier materials to produce a single dosage form will vary depending upon the host treated and the particular mode of administration.

For example, a formulation intended for the oral administration of humans may contain from 5 mg to 500 mg of each active agent(s) compounded with an appropriate and convenient amount of carrier material which may vary from about 5 to about 95 percent of the total composition. For purposes of this specification, this broad dosage range is specifically intended to include, but is not limited to, range of 5 mg to 500 mg; 5 mg to 250 mg; 10 mg to 500 mg; 10 mg to 250 mg; 25 mg to 500 mg; and 25 mg to 250 mg. It is further anticipated that an adult may be administered up to 500 mg of elastase inhibitor per day. This daily dosage may be divided into 2 or three doses per day. Examples of such doses include, 2.5, 5, 10, 12.5, 25, 50, 100, 125, and 250 mg administered twice a day.

Furthermore, it is also possible that most effective treatment may warrant administration of an initial dosage of one range (e.g. 250 mg or 500 mg in a dose) followed by administration of a second (lower) range (e.g. 2.5, 5, 10, 12.5, 25, 50, 100, 125) twice a day.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A method of treating cyclic or severe congenital neutropenia, in a patient in need of such treatment comprising administering a therapeutically effective amount of a compound of Formula (I)

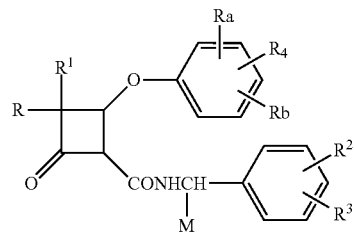

or a pharmaceutically acceptable salt thereof wherein
$R^1$ is $C_{1-6}$ alkyl or $C_{1-6}$ alkoxy-$C_{1-6}$alkyl;
M is
(1) hydrogen,
(2) $C_{1-6}$alkyl,
(3) hydroxy $C_{1-6}$alkyl,
(4) halo $C_{1-6}$alkyl,
(5) $C_{2-6}$alkenyl, or
(6) $C_{1-6}$alkoxy-$C_{1-6}$alkyl;
Ra and Rb are each individually
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) di-($C_{1-6}$alkyl)amino;
(9) hydroxy;
$R_2$ and $R_3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino$C_{2-3}$alkyloxy carbonyl wherein the amino is optionally mono or di-substituted with $C_{1-6}$alkyl,
(9) amino$C_{2-3}$alkylamino carbonyl wherein the amino is optionally mono or di-substituted with $C_{1-6}$ alkyl,
(10) hydroxy,
(11) aminocarbonyl wherein the amino is optionally mono or di-substituted with $C_{1-6}$alkyl,
(12) hydroxymethyl,
(13) aminocarbonyloxy $C_{1-3}$alkyloxy wherein the amino is optionally mono or di-substituted with $C_{1-6}$ alkyl,
(14) cyano,
(15) morpholinocarbonylphenyl,
(16) amino wherein the amino is optionally mono or di-substituted with $C_{1-6}$alkyl, with the proviso that $R_2$ and $R_3$ may be joined together to form a methylenedioxy group or a furan ring,
(17) morpholinocarbonyl;
R4 is
(a) Q-C(O)—Y—N(R7)(R8), or
(b) Q-C(O)—ORx, where Rx is carboxyC-16alkyl, benzyloxycarbonyl$C_{1-3}$ alkyl, or t-butoxycarbonyl$C_{1-3}$ alkyl, wherein
Q is a covalent bond or —C($R_5$)($R_6$)—
wherein $R_5$ and $R_6$ are each individually $C_{1-3}$ alkyl or hydrogen, Y is

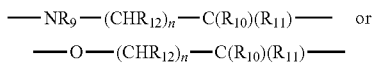

or a covalent bond;
$R_{12}$ is hydrogen or $C_{1-3}$alkyl;
$R_7$ and $R_8$ are each individually
(a) hydrogen,
(b) $C_{1-6}$alkyl,
(c) $C_{1-6}$alkyloxy $C_{2-3}$alkyl,
(d) hydroxy $C_{2-6}$alkyl,
(e) polyhydroxy$C_{2-6}$alkyl,
(f) carboxamido $C_{1-6}$alkyl,
(g) polyacyloxy$C_{2-6}$alkyl
(h) $C_{1-6}$alkanoyl,
(i) substituted phenyl or phenyl $C_{1-6}$alkyl, wherein the substitutent is $X_1$ as defined immediately below,
(j) $C_{2-6}$alkenyl,
(k) $C_{6-10}$cycloalkenyl,
(l) heteroaryl $C_{1-6}$alkyl wherein the hetero aryl includes pyridinyl, imidazolyl, triazolyl, benzylimidazolyl, and furyl,
(m) carboxy $C_{1-6}$alkyl,
(n) carbo $C_{1-6}$alkoxy $C_{1-3}$alkyl,
(o) phenylsulfonyl,
(p) $C_{1-6}$alkylsulfonyl,
(q) benzyloxy,
(r) morpholinyl $C_{1-3}$alkylsulfonyl,
(s) tetrahydropyranyl,
(t) amino$C_{1-3}$alkylsulfonyl wherein the amino is optionally mono or di-substituted with $C_{1-6}$alkyl,
(u) aminocarbonyl wherein the amino is optionally mono or di-substituted with $C_{1-6}$ alkyl,
(v) aminocarbonyloxy$C_{2-6}$alkyl wherein the amino is optionally mono or di-substituted with $C_{1-6}$alkyl,
(w) azabicyclo of 7 to 12 atoms,
(x) di $C_{1-3}$alkylamino $C_{2-6}$alkyl wherein the amino is optionally mono or di-substituted with $C_{1-6}$alkyl,
(y) bicycloalkyl of 7 to 12 atoms,
(z) $C_{3-10}$cycloalkyl optionally substituted with $C_{1-6}$alkyl,
(aa) pyrazolidinyl,
(bb) substituted piperidinyl or pyrrolidinyl wherein the substitutent is hydrogen, $C_{1-3}$ alkyl, hydroxy$C_{1-3}$ alkyl-benzyl, carboxamido or amino wherein the amino is optionally mono or di-substituted with $C_{1-6}$ alkyl,
(cc) substituted pyrrolidinyl wherein the substitutent is carboxamido or amino wherein the amino is optionally mono or di-substituted with $C_{1-6}$alkyl,
(dd) pyrimidinyl,
(ee) N-cyano-N'-phenylamidino,
(ff) phosphono$C_{1-6}$alkyl, or
(gg) α-$C_{1-3}$alkyl benzyl or mono or di-substituted benzyl or mono or di-substituted pyridylmethyl, wherein the substitutents are $X_1$ and $X_2$,
wherein
$X_1$ is
(1) hydrogen,
(2) halo,
(3) $C_{1-6}$alkyl,
(4) halo-$C_{1-6}$alkyl,
(5) $C_{2-6}$alkenyl,
(6) hydroxy-$C_{1-6}$alkyl,
(7) $C_{1-6}$alkylcarbonyl,
(8) $C_{1-6}$alkylcarbonylamino;
(9) CN,
(10) $CF_3$,
(11) $CH_3O$,
(12) amino wherein the amino is optionally mono or di-substituted with $C_{1-6}$ alkyl;
(13) carboxy, or
(14) phenylsulfonylaminocarbonyl;
$X_2$ is hydrogen, halo or $C_{1-6}$alkyl;
n is 1, 2, 3, 4 or 5;
$R_9$ is selected from hydrogen, $C_{1-4}$-alkyl, and $C_{1-3}$alkoxy$C_{1-3}$alkyl; or phenyl, phenyl $C_{1-3}$alkyl, pyridyl, and pyridyl $C_{1-3}$alkyl;
$R_{10}$ and $R_{11}$ are each independently selected from hydrogen, $C_{1-4}$alkyl, and $C_{1-3}$ alkoxy$C_{1-3}$alkyl, or aryl as defined above, or are together oxo; or
wherein $R_7$ and $R_8$ are joined together to form mono or di-substituted ring of 4, 5, 6, or 7 atoms or 7 to 12 atoms such as
(1) piperidinyl or homopiperidinyl,
(2) piperazinyl,
(3) morpholinyl, thiomorpholinyl or 1,1-dioxo-4-thiomorpholinyl,
(4) pyrroylidinyl,
(5) pyrryl,
(6) imidazolyl,
(7) triazolyl,
(8) saturated azabicyclo of 7 to 12 atoms,
(9) azaspiro having 3 to 9 carbon atoms, said ring being saturated,
(10) tetrazolyl,
(11) pyrazolidinyl,
(12) dihydrodimethozyisoquinolyl,
(13) azetidinyl, or
(14) diazabicyclo ring of 7-12 atoms,
wherein the substituents are each selected from the group consisting of hydrogen and $C_{1-3}$alkyl, benzyloxycarbonyl, carboxy, phenyl $C_{1-3}$alkyl amino carbonyl, pyrrolidinylmethyl, hydroxy $C_{1-3}$ alkyl, $C_{1-6}$ alkyloxy, $C_{1-4}$-alkyloxy carbonyl, aminocarbonyl wherein the amino is optionally mono or di-substituted with $C_{1-6}$ alkyl, and oxo; or
—N(R7)R8 may be an amino acid residue including natural amino acids such as lysine; or $R_8$ and $R_9$ are joined together to form a mono or di-substituted saturated monocyclic ring of 6 to 7 atoms and having two hetero atoms which are the nitrogens to which $R_8$ and $R_9$ are attached;
said rings to include piperazinyl and homopiperazinyl; or $R_9$ and $R_{10}$ are joined together to
form a mono or di-substituted monocyclic saturated ring of 5 to 7 atoms and having one hetero atom which is the nitrogen to which $R_9$ is attached; or
wherein $R_9$ and $R_{12}$ are joined together to form a mono or di-substituted saturated monocyclic ring of 5, 6; or 7 atoms, said ring having one hetero atom which is the nitrogen to which $R_9$ is attached; or wherein $R_{10}$ and $R_{12}$ are joined together to form a mono or di-substituted saturated monocyclic ring of 5, 6, or 7 carbon atoms; or
wherein $R_8$ and $R_{11}$ are joined together to form a mono or di-substituted saturated monocyclic ring of 5, 6, or 7 atoms, said ring having one hetero atom which is the nitrogen to which $R_8$ is attached; and the substituents are independently selected from Hydrogen and $C_{1-3}$alkyl, thereby treating cyclic or severe congenital neutropenia in a patient in need of such treatment.

2. The method according to claim 1 where wherein
R is $C_{1-6}$alkyl;
$R_1$ is $C_{1-6}$alkyl or $C_{1-6}$alkoxy-$C_{1-6}$alkyl;
M is
(1) hydrogen,
(2) $C_{1-6}$alkyl,
(3) hydroxy $C_{1-6}$ alkyl,
(4) halo $C_{1-6}$alkyl,
(5) $C_{2-6}$alkenyl, or
(6) $C_{1-6}$ alkoxy-$C_{1-6}$alkyl;
Ra is
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di-substituted with $C_{1-6}$alkyl;
Rb is hydrogen, or $C_{1-6}$alkyl,
$R^2$ and $R^3$ are each independently
(1) hydrogen,
(2) $C_{1-6}$alkyl,
(3) halo,
(4) carboxy,
(5) $C_{1-6}$alkoxy,
(6) phenyl,
(7) $C_{1-6}$alkylcarbonyl,
(8) amino wherein the amino is optionally mono or di-substituted with $C_{1-6}$alkyl, or with the proviso that $R^2$ and $R^3$ may be joined together to form a methylenedioxy group or a furan ring;
$R^4$ is
(a) Q-C(O)—Y—N($R^7$)($R^8$), or
(b) Q-C(O)—ORx, where Rx is carboxy-C-16alkyl, benzyloxycarbonyl$C_{1-3}$ alkyl, or t-butoxycarbonyl$C_{1-3}$ alkyl,
wherein
Q is a covalent bond or —C($R_5$)($R_6$)—
wherein $R_5$ and $R_6$ are each individually $C_{1-3}$ alkyl or hydrogen,
Y is —NR$_9$—(CHR$_{12}$)$_n$—C(R$_{10}$)(R$_{11}$)—   or —O—(CHR$_{12}$)$_n$—C(R$_{10}$)(R$_{11}$)— or a covalent bond;
$R_{12}$ is hydrogen or $C_{1-3}$alkyl;
$R_7$ and $R_8$ are each individually
(a) hydrogen,
(b) $C_{1-6}$alkyl,
(c) $C_{1-6}$alkyloxy $C_{2-3}$alkyl,
(d) hydroxy $C_{2-6}$alkyl,
(e) carboxamido $C_{1-6}$alkyl,
(f) $C_{1-6}$alkanoyl,
(g) substituted phenyl or phenyl $C_{1-6}$alkyl wherein the substituents are $X_1$, and $X_2$,
(h) $C_{2-6}$alkenyl,
(i) $C_{6-10}$cycloalkenyl,
(j) heteroaryl $C_{1-6}$ alkyl wherein the hetero aryl includes pyridinyl, imidazolyl, triazolyl, benzylimidazolyl, and furyl,
(k) carboxy $C_{1-6}$ alkyl,
(l) $C_{1-6}$alkylsulfonyl,
(m) carbo$C_{1-6}$ alkyloxy$C_{2-3}$alkyl,
(n) morpholinyl $C_{1-3}$alkylsulfonyl,
(o) amino$C_{1-3}$alkylsulfonyl wherein the amino is optionally mono or di-substituted with $C_{1-6}$alkyl,
(p) aminocarbonyl wherein the amino is optionally mono or di-substituted with $C_{1-6}$ alkyl,
(q) aminocarbonyloxy$C_{1-6}$alkyl wherein the amino is optionally mono or di-substituted with $C_{1-6}$alkyl,
(r) di $C_{1-3}$alkylamino $C_{1-6}$ alkyl wherein the amino is optionally mono or di-substituted with $C_{1-6}$alkyl,
(s) pyrazolidinyl,
(t) substituted piperidinyl as defined above,
(u) substituted pyrrolidinyl as defined above,
(v) pyrimidinyl,
(w) benzyloxy,
(x) $C_{3-10}$cycloalkyl,
(z) α-$C_{1-3}$ alkyl benzyl or mono or di-substituted benzyl or mono or di-substituted pyridylmethyl, wherein the substitutents are $X_1$ and $X_2$,
wherein
$X_1$ is
(1) hydrogen,
(2) halo,
(3) $C_{1-6}$alkyl,
(4) halo-$C_{1-6}$alkyl,
(5) C2-6alkenyl,
(6) hydroxy-$C_{1-6}$alkyl,
(7) $C_{1-6}$alkylcarbonyl,
(8) $C_{1-6}$alkylcarbonylamino;
(9) di-$C_{1-3}$alkylamino; or
(10) carboxy,
$X_2$ is hydrogen, halo or $C_{1-6}$alkyl;
n is 1, 2, 3, 4 or 5;
$R_9$ is selected from hydrogen, $C_{1-4}$alkyl, and $C_{1-3}$alkoxy$C_{1-3}$alkyl; $R_{10}$ and $R_{11}$ are each independently selected from hydrogen, $C_{1-4}$alkyl, and $C_{1-3}$alkoxy $C_{1-3}$alkyl; or
wherein $R_7$ and $R_8$ are joined together to form mono or di-substituted ring of 4, 5, 6, or 7 atoms such as
(1) piperidinyl,
(2) piperazinyl,
(3) morpholinyl,
(4) pyrroylidinyl,
(5) pyrryl,
(6) imidazolyl,
(7) triazolyl,
(8) tetrazolyl,
(9) pyrazolidinyl,
(10) azetidinyl,
wherein the substituents are each selected from the group consisting of hydrogen and $C_{1-3}$alkyl, benzyloxycarbonyl, carboxy, phenyl $C_{1-3}$alkyl amino carbonyl, pyrrolidinyl, methyl, hydroxy $C_{1-3}$alkyl, $C_{1-6}$alkyloxy, $C_{1-4}$alkyloxy carbonyl, and oxo; or $R_8$ and $R_9$ are joined together to form a saturated ring of 5 to 7 atoms and having two hetero atoms; or $R_9$ and $R_{10}$ are joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or wherein $R_8$ and $R_{11}$ are joined together to form a ring of 5, 6, or 7 atoms, said ring being saturated and having one hetero atom.

3. The method according to claim 1 wherein
R is $C_{1-3}$alkyl;
$R_1$ is $C_{1-3}$alkyl;
M is
(a) $C_{1-6}$alkyl, or
(b) $C_{2-6}$ alkenyl;
$R_2$ is
(a) hydrogen,
(b) $C_{1-6}$ alkyl, or $C_{1-6}$alkoxy, and
$R_3$ is hydrogen, or $R_2$ and $R_3$ are joined together to form a methylenedioxy group or a furan ring;
$R_5$ and $R_6$ are each individually hydrogen or $C_{1-3}$alkyl;
$R_7$ and $R_8$ are each independently selected from
(a) hydrogen,
(b) $C_{1-3}$alkyl,
(c) $C_{1-3}$ alkoxy $C_{2-3}$alkyl,
(d) $C_{3-7}$cycloalkyl,
(e) hydroxy$C_{2-3}$alkyl,
(d) carbo $C_{1-4}$alkyloxymethyl,
(g) substituted benzyl wherein the substituents are $X_1$ and $X_2$
wherein $X_1$ is hydrogen and $X_2$ is
(1) hydrogen,
(2) halo, or
(3) $C_{1-3}$alkyl;
n is 1, 2 or 3, and
$R_9$, $R_{10}$ and $R_{11}$ are each independently selected from hydrogen, $C_{1-4}$alkyl, and $C_{1-3}$alkoxy $C_{1-3}$alkyl; or
$R_7$ and $R_8$ are joined together to form a substituted ring selected from
(a) piperidinyl,
(b) piperazinyl, and
(c) morpholinyl;
or
$R_8$ and $R_9$ are joined together to form a ring of 6 to 7 atoms and having two hetero atoms; $R_9$ and $R_{10}$ are joined together to form a saturated ring of 5 to 7 atoms and having one hetero atom; or wherein $R_9$ and $R_{12}$ are joined together to form a ring of 5, 6, or 7 atoms, said ring being saturated; or wherein $R_{10}$ and $R_{12}$ are joined together to form a ring of 5, 6, or 7 atoms, said ring being saturated; or
wherein $R_8$ and $R_{11}$ are joined together to form a ring of 5, 6, or 7 atoms, said ring being saturated and having one hetero atom.

4. The method of treating cyclic or severe congenital neutropenia in a patient in need of such treatment comprising the administration of a compound according to claim 3.

5. The method according to claim 1 wherein
Q is a covalent bond;
R is methyl or ethyl;
$R^1$ is methyl or ethyl;
M is
(a) $C_{1-4}$alkyl, or
(b) $C_{2-3}$alkenyl;
$R^2$ is
(a) hydrogen,
(b) $C_{1-3}$ alkyl, or $C_{1-3}$alkoxy, and
$R^3$ is hydrogen, or
$R^2$ and $R^3$ are joined together to form a furan or dioxacyclopentane ring;
n is 1 or 2;
$R_9$ and $R_{10}$ are each independently selected from
(a) $C_{1-3}$ alkyl,
(b) $C_{1-3}$alkoxy $C_{1-3}$alkyl,
(c) hydrogen, $R_7$ and $R_8$ are each independently selected from
(a) $C_{1-3}$alkyl,
(b) $C_{1-3}$alkoxy $C_{2-3}$alkyl,
(c) hydrogen,
(d) hydroxyethyl,
(e) carboethoxymethyl,
(f) cyclopropyl,
or
$R_7$ and $R_8$ are joined together to form a substituted ring selected from
(a) piperidinyl, and
(b) morpholinyl, or
$R_8$ and $R_9$ are joined together to form a piperazine ring.

6. The method of treating cyclic or severe congenital neutropenia in a patient in need of such treatment comprising the administration of a compound according to claim 5.

7. The method according to claim 1 wherein the severe neutropenia is cyclic neutropenia (CN) or severe congenital neutropenia (SCN).

8. A method of treating cyclic or severe congenital neutropenia, in a patient in need of such treatment comprising administering a therapeutically effective amount of a compound of Formula Ia

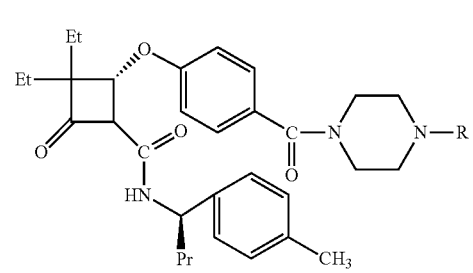

Ia or a pharmaceutically acceptable salt thereof, wherein
R is selected from the group

| No. | R |
|---|---|
| 242 | —CH3 |
| 243 | 4-fluorophenyl |
| 244 | 3-chlorophenyl |
| 245 | Phenyl |
| 246 | Benzyl |
| 247 | H |
| 248 | i-propyl |
| 249 | i-butyl |
| 250 | —CH$_2$CO$_2$Et |
| 251 | —CH$_2$CO$_2$H |
| 252 | Et |
| 253 | Pr |
| 254 | 2-pyrimidinyl |
| 255 | —CH$_2$CH$_2$OC(O)NHCH$_3$ |
| 256 | Cyclopropyl |
| 256a | —CH$_2$CH$_2$OH | thereby treating cyclic or severe congenital neutropenia, in a patient in need of such treatment.

9. A method of treating cyclic or severe congenital neutropenia, in a patient in need of such treatment comprising administering a therapeutically effective amount of a compound of Formula Ib

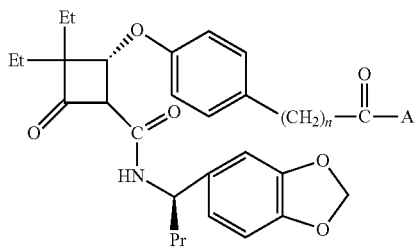

or a pharmaceutically acceptable salt thereof, wherein

| No. | n | R |
|---|---|---|
| 257 | 1 | —NH$_2$ |
| 258 | 1 | 4-morpholinyl |
| 259 | 1 | —N(CH$_3$)CH$_2$CH$_2$N(CH$_3$)$_2$ |
| 260 | 0 | —N(CH$_3$)CH$_2$CH$_2$N(CH$_3$)$_2$ |
| 261 | 0 | —N(Et)$_2$ |
| 262 | 0 | —N(CH$_3$)(n-butyl) |
| 263 | 0 | 4-methyl-1-piperazinyl |
| 264 | 0 | —N(CH$_3$)CH$_2$CH$_2$N(CH$_3$)CH$_2$Ph |
| 265 | 0 | —CH$_2$CO$_2$Et |
| 265a | 0 | 1-piperazinyl |
| 265c | 0 | 4-(2-hydroxyethyl)-1-piperazinyl |
| 265d | 0 | 4-morpholinyl | thereby treating cyclic or severe congenital neutropenia, in a patient in need of such treatment.

* * * * *